United States Patent
Knauf et al.

(10) Patent No.: US 9,309,184 B2
(45) Date of Patent: Apr. 12, 2016

(54) METHOD FOR PRODUCING DIAMINES AND POLYAMINES OF THE DIPHENYLMETHANE SERIES

(71) Applicant: Covestro Deutschland AG, Leverkusen (DE)

(72) Inventors: Thomas Knauf, Dormagen (DE); Wolfgang Lorenz, Dormagen (DE); Stefan Wershofen, Monchengladbach (DE); Richard Adamson, Leichlingen (DE); Karsten Becker, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/782,926

(22) PCT Filed: Apr. 9, 2014

(86) PCT No.: PCT/EP2014/057116
§ 371 (c)(1),
(2) Date: Oct. 7, 2015

(87) PCT Pub. No.: WO2014/166977
PCT Pub. Date: Oct. 16, 2014

(65) Prior Publication Data
US 2016/0068475 A1    Mar. 10, 2016

(30) Foreign Application Priority Data
Apr. 11, 2013  (EP) .................................... 13163356

(51) Int. Cl.
| C07C 209/86 | (2006.01) |
| C07C 209/78 | (2006.01) |
| C07C 209/68 | (2006.01) |
| B01D 17/00 | (2006.01) |
| C07C 263/10 | (2006.01) |

(52) U.S. Cl.
CPC .............. *C07C 209/86* (2013.01); *B01D 17/08* (2013.01); *C07C 209/68* (2013.01); *C07C 209/78* (2013.01); *C07C 263/10* (2013.01)

(58) Field of Classification Search
CPC .. C07C 209/60; C07C 209/86; C07C 209/78; C07C 209/68
See application file for complete search history.

(56) References Cited

U.S. PATENT DOCUMENTS

| 5,286,760 A | 2/1994 | Bolton et al. |
| 6,433,219 B1 | 8/2002 | Strofer et al. |
| 6,576,788 B1 | 6/2003 | Penzel et al. |
| 6,987,165 B2 | 1/2006 | Auer et al. |
| 7,230,130 B2 | 6/2007 | Strofer et al. |
| 7,253,321 B2 | 8/2007 | Hagen et al. |
| 7,312,362 B2 | 12/2007 | Keggenhoff et al. |
| 7,528,283 B2 | 5/2009 | Pohl et al. |
| 2006/0094897 A1 | 5/2006 | Muller et al. |
| 2009/0240077 A1 | 9/2009 | Wershofen et al. |
| 2013/0310616 A1 | 11/2013 | Neumann et al. |

FOREIGN PATENT DOCUMENTS

| DE | 844896 | 4/1944 |
| EP | 0451442 | 4/1990 |
| EP | 2103595 A1 * | 9/2009 |

OTHER PUBLICATIONS

Twitchett, H.J., Chem. Soc. Rev. 3(2), p. 223 (1974).
Muller, E. et al., Ullmann's Encyclopedia of Industrial Chemistry, vol. 21, pp. 272-274, 2012, Wiley-VCH Verlag GmbH & Co., KGaA.
Kirk-Othmer Encyclopedia of Chemical Technology, Jun. 15, 2007, pp. 22-23.

* cited by examiner

*Primary Examiner* — Paul A Zucker
(74) *Attorney, Agent, or Firm* — N. Denise Brown; Donald R. Palladino

(57) ABSTRACT

The invention relates to a method for producing diamines and polyamines of the diphenylmethane series, wherein first aniline and formaldehyde are reacted in the absence of an acidic catalyst to form a reaction mixture containing animal and water and, after the water has been separated the aminal is reacted by acid catalysis to form a reaction mixture containing diamines and polyamines of the diphenylmethane series, wherein the separation of the water from the aminal is supported by the use of a coalescence aid. According to the invention, a filter bed made front coalescence fiber material is used an coalescence aid.

9 Claims, No Drawings

METHOD FOR PRODUCING DIAMINES AND POLYAMINES OF THE DIPHENYLMETHANE SERIES

CROSS-REFERENCE TO RELATED APPLICATIONS

This Application is a National Phase Application of PCT/EP201/057116, filed Apr. 9, 2014, which claims priority to European Application No. 13163356.2, filed Apr. 11, 2013, each of which being incorporated here in by reference.

FIELD

The invention relates to a process for the preparation of di- and polyamines of the diphenylmethane series in which firstly aniline and formaldehyde are converted in the absence of an acidic catalyst to a reaction mixture comprising aminal and water and, after separating off the water, the aminal is converted by acid catalysis to a reaction mixture comprising di- and polyamines of the diphenylmethane series, in which the separation of the water from the aminal is assisted using a coalescence auxiliary. According to the invention, the coalescence auxiliary used is a filter bed of coalescence fiber material.

BACKGROUND

The preparation of di- and polyamines of the diphenylmethane series (MDA) by conversion of aniline with formaldehyde in the presence of acidic catalysts is generally known. In the context of the present invention, di- and polyamines of the diphenylmethane series are understood as meaning amines and mixtures of amines of the following type:

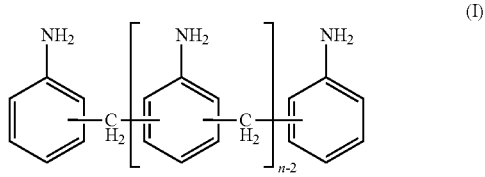

(I)

Here, n is a natural number >2. Hereinbelow, the compounds of this type in which n=2 are referred to as diamines of the diphenylmethane series or diaminodiphenylmethanes (subsequently MMDA). Compounds of this type in which n is >2 are referred to within the context of this invention as polyamines of the diphenylmethane series or polyphenylene-polymethylenepolyamines (subsequently PMDA). Mixtures of both types are referred to as di- and polyamines of the diphenylmethane series (subsequently MDA). The corresponding isocyanates, which can be derived formally by replacing all $NH_2$ groups by NCO groups from the compounds of formula (I) are accordingly referred to as diisocyanates of the diphenylmethane series (subsequently MMDI), polyisocyanates of the diphenylmethane series or polyphenylenepolymethylenepolyisocyanates (subsequently PMDI) or di- and polyisocyanates of the diphenylmethane series (subsequently MDI). Here, both in the case of the amine and also in the case of the isocyanate, the polymer (n>2) is generally always present in the mixture with the dimer (n=2), meaning that in practice only two compound types are relevant, the pure dimers (MMDA or MMDI) and the mixture of dimers and polymers (MDA or MDI).

Industrially, the di- and polyamine mixtures are converted predominantly by phosgenation to the corresponding di- and polyisocyanates of the diphenylmethane series. The continuous or partly discontinuous preparation of MDA is disclosed, e.g., in U.S. Pat. No. 5,286,760, EP-A-451442 and WO-A-99/40059.

The work-up of the acidic reaction mixture obtained in the preparation is triggered according to the prior art by neutralization with a base. According to the prior art, the neutralization usually takes place at temperatures of for example 90° C. to 100° C. without the addition of further substances (H. J. Twitchett, Chem. Soc. Rev. 3(2), p. 223 (1974)). However, it can also take place at a different temperature level in order e.g. to increase the rate of the degradation of troublesome by-products. Hydroxides of the alkali metal and alkaline earth metal elements are suitable as bases. Preferably, aqueous NaOH is used.

After the neutralization, the organic phase is separated from the aqueous phase in a separation container. The organic phase comprising crude MDA which remains after the aqueous phase has been separated off is subjected to further work-up steps such as e.g. a washing with water (base washing) in order to wash residual salts from the crude MDA. Finally, the crude MDA purified in this way is freed from excess aniline, water and other substances present in the mixture (e.g., further solvents) by suitable methods such as e.g. distillation, extraction or crystallization. The work-up customary according to the prior art is disclosed for example in EP 1 652 835 A1, page 3, line 58 to page 4, line 13 and EP 2 103 595 A1, page 7, lines 21 to 37.

EP 1 616 890 A1 discloses a process in which aniline and formaldehyde are firstly converted in the absence of the acidic catalyst to aminal, and the aminal obtained in this way is then admixed with an acidic catalyst and converted further at temperatures of 20° C. to 100° C. and at water contents of the acidic reaction mixture obtained in this way of 0 to 20 percent by weight. In particular, after the condensation of formaldehyde and aniline to give the aminal, firstly the water is at least partly removed from the aminal, with a water content of 0 to 5 percent by weight being established in the aminal before the aminal is admixed with acidic catalyst. In this way, it is possible to prepare MDA with a degree of protonation of <15%, preferably 4% to 14%, particularly preferably 5% to 13%. The degree of protonation here for monobasic acidic catalysts (such as hydrochloric acid) is the term used to refer to the molar ratio of the amount of acidic catalyst used and the molar amount of amine functions present in the reaction mixture.

EP 1 813 598 A1 teaches (see in particular paragraphs [0037] to [0042]) that the water of reaction produced in the aminal reaction is partly removed and combined with other waste water streams of the process and is further treated to remove organic constituents, such as e.g. aniline and MDA, such as e.g. a combination of extraction and distillation. The whereabouts of the feed material formalin is not described.

The quality of a process for the preparation of MDA is on the one hand defined by the content in the product of undesired byproducts of the reaction. On the other hand, the quality of a continuous process is defined by the fact that the overall process from start-up, normal production to shutdown of the process can be operated without technical production loss or problems which require intervention in the process, and that there are no resulting losses of feed materials, intermediate products or end product. Such problems can arise e.g. upon adjusting the water content in the aminal by phase separation of organic phase and aqueous phase. Problems of this type can be e.g. that it results in delays during phase separation, or that the phase separation is incomplete, or that a third phase (mulm or mulm layer) is formed. This third phase is a stable, sometimes voluminous interim phase which occurs between the aqueous phase and the organic phase and hinders the phase separation and, in extreme cases, even prevents it entirely. In the most unfavorable case for operational progress, the phase separation container or containers affected have to be completely emptied and cleaned. The content of the phase separation container or containers then has to be worked up, which is complex, or be disposed of, which is associated with considerable costs. In some circumstances, this can also lead to the continuous production having to be interrupted. If the formation of a mulm layer cannot be completely avoided, then this will ultimately end up in one of the two phases. If the mulm layer ends up in the organic phase, then, in the case of phase separation after the aminal reaction, this is less serious than if it ends up in the aqueous phase. This is because in the last-mentioned case, larger amounts of dispersely dissolved organic materials then end up in the aminal water with the mulm layer. Said losses can then arise during the disposal or further use of the aminal water.

It would therefore be desirable to have available processing measures in order to be able to overcome these problems.

EP 2 103 595 A1 deals with a procedure for the preparation of di- and polyamines of the diphenylmethane series in which aniline and formaldehyde are converted in the presence of an acidic catalyst. In connection with the phase separation after the neutralization of the crude product, it is disclosed that this phase separation can be assisted by adding water and/or aniline. Preferably, the reaction mixture diluted by adding water and/or aniline is separated into an organic phase and aqueous phase in separating flasks with plate sections, assisting the coalescence of the two phases, as internals (paragraphs [0043] and [0044]). Completely satisfactory results cannot be achieved with plate sections if particularly high requirements are placed on the quality of a phase separation. This was not acknowledged in EP 2 103 595 A1.

Although the described processes of the prior art succeed in preparing MDA with a high yield, no technical auxiliaries are described which could improve the separation of the organic phase from the aqueous aminal phase with the desirable efficacy in order to minimize the losses of feed materials and intermediate products in the reaction process and to ensure a seamless technical progress of the production process.

There was thus a need for a process for the preparation of di- and polyamines of the diphenylmethane series in which it is possible, by means of simple measures, to conduct an improved phase separation between organic phase and aqueous phase in the aminal stage. This would improve the cost-effectiveness of existing MDA processes.

SUMMARY

Taking into account that stated above, the present invention provides a process for the preparation of di- and polyamines of the diphenylmethane series in which
  a) aniline and formaldehyde are converted in the absence of an acidic catalyst to a reaction mixture comprising aminal and water,
  b) water, which consists essentially of water of condensation of the aminal reaction and water from the feed material formaldehyde, is removed at least in part from the reaction mixture obtained in step a), giving an organic phase (1) comprising the aminal,
  c) the organic aminal-comprising phase (1) obtained in step b) is converted in the presence of an acidic catalyst, giving a reaction mixture comprising di- and polyamines of the diphenylmethane series,
  d) the reaction mixture comprising di- and polyamines of the diphenylmethane series obtained in step c) is neutralized and then subjected to a work-up involving washing and distillation,
wherein, the purposes of the separation of the water from the reaction mixture obtained in step a),
  b.1) the reaction mixture obtained in step a) is separated in a separating container into an aqueous and an organic phase (1a), and then
  b.2) the aqueous phase obtained in step b.1) (the so-called "aminal water")
    (i) is passed through a coalescence auxiliary and
    (ii) is then separated into an aqueous phase and an organic phase (1b), and then
  b.3) the organic phase (1b) obtained in step b.2) is combined with the organic phase (1a) obtained in step b.1) to give the organic phase (1).

The invention also relates to a process for the preparation of di- and polyisocyanates of the diphenylmethane series in which di- and polyamines of the diphenylmethane series are prepared by the process according to the invention and are then converted with phosgene to the corresponding di- and polyisocyanates.

DETAILED DESCRIPTION

Embodiments of the invention are described in more detail below. Different embodiments can be combined with one another as desired provided the opposite does not clearly arise for the person skilled in the art from the context.

The condensation of aniline and formaldehyde in step a) can be carried out by a process according to the prior art. Here, preferably aniline and aqueous formaldehyde solution are condensed at a molar ratio of aniline to $CH_2O$ of 1.7:1 to 20:1, preferably 1.7:1 to 5.0:1 at a temperature of 20° C. to 100° C., preferably from 30° C. to 95° C., particularly preferably from 40° C. to 90° C., to give aminal and water. The conversion usually takes place at atmospheric pressure. Suitable aniline grades are described e.g. in EP 1 257 522 B1, EP 2 103 595 A1 and EP 1 813 398 B1. Preference is given to using technical grades of formalin (aqueous solution of formaldehyde) with 30% by mass to 50% by mass of formaldehyde in water. However, formaldehyde solutions with lower or higher concentrations or else the use of gaseous formaldehyde are also conceivable.

In step b) the phase separation of organic aminal phase (1.a) and aqueous phase (step b.1) takes place at a temperature of 20° C. to 100° C., preferably from 30° C. to 95° C., particularly preferably from 40° C. to 90° C., preferably at ambient pressure. Optimization of this phase separation takes place by using a filter bed of coalescence fiber material as coalescence auxiliary in step b.2). Here, the organic fraction in the aminal water separated after the aminal reaction is minimized (clarification of the residual cloudiness). The thus separated organic fraction (1.b) is combined with the organic phase (1.a) obtained in steps b.1) to give the organic phase (1).

The separation off of the organic constituents (1.b) from the aqueous phase (aminal water) takes place according to the invention by using as filter bed of coalescence fiber material as coalescence auxiliary. The choice of fiber material is dependent, inter alia, on:
  wetting properties of the disperse phase (drops) from the fiber material, the interfacial tension of the substance system,
the viscosity of the two phases of the substance system.

The finely disperse organic droplets must be able to wet the surface of the fiber material.

Upon passage of the liquid-liquid dispersion (organic constituents dispersed in the aminal water) through the fiber material, the organic droplets, present in finely disperse form, are able to wet the fiber surface. The organic droplets collect on the fibers (drop-fiber coalescence), after further fiber coating the distances between the attached small droplets decrease, and ultimately the droplets combine to give larger drops (drop-drop coalescence). Upon exceeding a characteristic limiting drop diameter (dependent on the substance system, viscosity, flow conditions), the now enlarged drops become detached as a result of the flow forces within the fiber bed and leave the fiber material as considerably enlarged drops compared to the entry drops. On account of the improved sedimentation properties, these organic drops can be deposited in the subsequent phase separation in the earth's gravitational field, which leads to a minimization of the residual cloudiness of the aminal water.

Success during the separation task depends on a formation of gas bubbles being avoided, which requires a process procedure at temperatures below the boiling point of the disperse system and the individual resulting phases and excludes the use of inert gases. Consequently, the separation task for the system according to the invention (step (b.2(i)) is carried out in the temperature range preferably from 50° C. to 120° C., particularly preferably from 70° C. to 115° C. and very particularly preferably from 75° C. to 110° C. For the separation task, the pressure in the separating system is chosen such that boiling of the disperse system does not occur. The minimum pressure to be set depends on the temperature level and the composition of the disperse system and can be ascertained through simple experiments. Preferably, the separation task is carried out at atmospheric pressure ranging to an increased pressure of 10 bar absolute, preferably up to 5 bar absolute, particularly preferably up to 2 bar absolute.

The fiber diameter of the coalescence fiber material is preferably from 1.0 μm to 150 μm, particularly preferably from 1.0 μm to 100 μm, very particularly preferably from 2.0 μm to 30 μm. The nominal pore size of the coalescence material is preferably 5 μm to 40 μm and particularly preferably 10 μm to 30 μm.

For the separation off of the organic droplets, present in disperse form, preference is given to using fibers made of a borosilicate glass material or organic polymer material, particularly preferably fibers made of an organic polymer material which is stable in the alkaline medium. Suitable organic polymer materials are, for example, polytetrafluoroethylene (PTFE), polytrifluoroethylene, polydifluoroethylene, copolymers of tetrafluoroethylene and/or trifluoroethylene and/or difluoroethylene with one another and with other monomers, derivatives of PTFE, polypropylene (PP) and polyethylene (PE). According to the invention, "derivatives of PTFE" are understood as meaning those polymer materials which comprise PTFE (e.g. composites with PTFE as one of the constituents) or are copolymers of tetrafluoroethylene with other monomers (e.g. poly(ethylene-co-tetrafluoroethylene) (ETFE)). In particular, the fluorine-containing polymer materials are exceptionally suitable for the use according to the invention, and indeed at all of the temperatures relevant in practice. Above a temperature of approx. 80° C., the fluorine-containing polymer materials are preferred over other polymer materials such as PP or PE. Very particular preference is given to using a material of polytetrafluoroethylene (PTFE) or derivatives thereof (in particular ETFE and composites containing PTFE or ETFE). The specific hydraulic load upon passage through the aminal water by the coalescence fiber material is preferably in the range $1.0\ m^3/(m^2h)$ to $10\ m^3/(m^2h)$, particularly preferably $1.0\ m^3/(m^2h)$ to $8.0\ m^3/(m^2h)$ and very particularly preferably $2.0\ m^3/(m^2H)$ to $6.0\ m^3/(m^2h)$.

The thickness of the filter bed according to the invention made of coalescence fiber material is preferably 1.0 mm to 100 mm, particularly preferably 1.0 mm to 50 mm and very particularly preferably 1.0 mm to 30 mm.

The rearrangement of the aminal in step c) takes place in the presence of an acidic catalyst, usually a strong mineral acid such as hydrochloric acid. Preference is given to the use of mineral acid in a molar ratio mineral acid:aniline of 0.001:1 to 0.9:1, preferably 0.05:1 to 0.5:1. It is naturally also possible to use solid, acidic catalysts as described in the literature. In this connection, formaldehyde can be added to a mixture of aniline and acidic catalyst and the reaction solution can be fully reacted by stepwise heating. Alternatively, aniline and formaldehyde can also firstly be prereacted and then be admixed, with or without prior water removal, with the acidic catalyst or a mixture of further aniline and acidic catalyst, after which the reaction solution is fully reacted by stepwise heating. This reaction can be carried out continuously or discontinuously with one of the numerous processes described in the literature (e.g. in EP 1 616 890 A1 or EP 127 0544 A1).

In step d) the reaction mixture comprising the di- and polyamines of the diphenylmethane series is firstly neutralized, optionally with the addition of water and/or aniline (step d.1)). The neutralization preferably takes place at a temperature of 90° C. to 100° C. without the addition of further substances. However, it can also take place at a different temperature level in order to increase the rate of e.g. the degradation of troublesome byproducts. Suitable bases are preferably the hydroxides of the alkali metal and alkaline earth metal elements. Preference is given to using sodium hydroxide solution. The base used for the neutralization is preferably used in an amount of more than 100%, particularly preferably 105% to 120%, of the amount required stoichiometrically for the neutralization of the acidic catalyst used (see EP 1 652 835 A1). The two-phase mixture obtained in this way is then separated into an organic phase comprising di- and polyamines of the diphenylmethane series and an aqueous phase. This can be assisted by the addition of aniline and/or water. If the phase separation is assisted by adding aniline and/or water, then their addition preferably already takes place with intensive mixing in the neutralization. In this connection, the mixing can take place in mixing sections with static mixers, in stirred tanks or stirred-tank cascades or else in a combination of mixing sections and stirred tanks. The neutralized reaction mixture, optionally diluted by adding aniline and/or water, is then preferably fed to an apparatus which, on account of its configuration and/or internals, is particularly suitable for separation into an organic phase comprising MDA and an aqueous phase, preferably phase separation or extraction devices corresponding to the prior art, as are described for example in Mass-Transfer Operations, 3rd Edition, 1980, McGraw-Hill Book Co, p. 477 to 541, or Ullmann's Encyclopedia of Industrial Chemistry (Vol. 21, Liquid-Liquid Extraction, E. Müller et al., pages 272-274, 2012 Wiley-VCH Verlag GmbH & Co, KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", Published Online: Jun. 15, 2007, pages 22-23) (mixer-settler cascade or settling container).

The organic phase obtained in this way is then subjected to a washing (step d.2)). The washing liquid used is preferably water. The wash water is then separated by means of phase separation. In this way, the salt content of the organic phase is reduced. A suitable process is described for example in DE-A-2549890, on page 3. The organic phase obtained in step d.2) preferably has a composition, based on the total mass of this organic phase, of 5.0% by mass to 15% by mass of water and, depending on use ratios of aniline and formaldehyde, 5.0% by mass to 90% by mass, preferably 5.0% by mass to 40% by mass, of aniline and 5.0% by mass to 90% by mass, preferably 50% by mass to 90% by mass, of di- and polyamines of the diphenylmethane series. After emerging from the phase separation in step d.2), the organic phase comprising di- and polyamines of the diphenylmethane series usually has a temperature of 80° C. to 150° C.

Then, water and aniline are separated off by distillation, as known in the prior art, from the resulting, neutralized and washed, organic phase comprising di- and polyamines of the diphenylmethane series (step d.3)). This takes place preferably as described in EP 1 813 597 B1, in particular in paragraphs [0014]0 to [0043].

The thus obtained di- and polyamines of the diphenylmethane series can be converted by the known methods with phosgene to the corresponding di- and polyisocyanates of the diphenylmethane series. In this connection, the phosgenation can be carried out by one of the processes known from the prior art (e.g. DE-A-844 896 or DE-A-198 17 691).

If the organic substance content of the aminal water is reduced with the aid of a filter bed of coalescence fiber material, and the thus obtained organic substances are further processed according to the invention, then the following advantages arise inter alia:
  i) The preparation costs of the process are improved because the losses of feed materials and intermediates via the aqueous phase are minimized.
  ii) The reduced loading of the aqueous phase with organic substances leads to a lower treatment cost in the waste water processing (energy costs are saved because less steam is required for stripping off organic substances from the MDA waste water).

EXAMPLE (ACCORDING TO THE INVENTION)

In a continuous reaction process (step a)), 243.4 t/h of "feed aniline" (90% by mass of aniline) and 6.1 t/h of 50% strength formaldehyde solution, which comprised 1.0% by mass of methanol, were mixed and converted continuously to the aminal at 95° C. in a stirred reaction vessel. The subsequent phase separation (step b.1)) in a phase separation apparatus proved difficult since the phase separation layer was difficult to see on account of clouding in the aqueous phase. The lower, aqueous phase was then passed in step b.2) through a coalescence auxiliary. The coalescence aid used was a coalescence fiber material made of an organic polymer material (PTFE) stable in alkaline medium. The fiber diameter of the material was 20 µm. 11 superimposed, perfused fiber tiles were used. The flow rate was 4 $m^3/(m^2h)$, i.e. 4 $m^3/h$ throughput, based on a through-flow cross sectional area of 1 $m^2$. The clarified aqueous phase was clear after passing through the fiber material. The residual cloudiness clarification by means of coalescence fiber material could be stably operated over a long production phase.

The organic phases from step b.1), the main phase separation, and from step b.2), the residual cloudiness clarification, were combined (step b.3)).

Following phase separation to remove the aqueous phase, the combined organic phases were admixed with 31% strength aqueous hydrochloric acid (degree of protonation 10%, i.e. 0.1 mol of HCl was added per mole of amino groups) and reacted at 50° C. to 150° C. in a reactor cascade (step c)). Following complete reaction, the resulting reaction mixture was admixed with 32% strength sodium hydroxide solution in the molar ratio of 1.1:1 sodium hydroxide solution to HCl and reacted in a neutralization stirred container (step d)). The temperature was 115° C. The absolute pressure was 1.4 bar. The neutralized base mixture was then separated in a neutralization separator into an aqueous, lower phase, which was passed to a waste water collecting container, and into an organic phase. The organic, upper phase was passed to the washing. In a stirred washing container, the alkaline MDA was washed with condensate. After separating off the wash water in a wash water separator, the crude MDA obtained in this way was freed from water and aniline by distillation, with 17 t/h of MDA being obtained as bottom product.

The invention claimed is:
1. A process for the preparation of di- and polyamines of the diphenylmethane series, comprising:
  a) converting aniline and formaldehyde in the absence of an acidic catalyst to a reaction mixture comprising aminal and water,
  b) removing water at least in part from the reaction mixture obtained in step a), giving an organic phase (1) comprising the aminal,
  c) converting the organic aminal-comprising phase (1) obtained in step b) in the presence of an acidic catalyst, giving a reaction mixture comprising di- and polyamines of the diphenylmethane series, and
  d) neutralizing the reaction mixture comprising di- and polyamines of the diphenylmethane series obtained in step c) and then subjecting the neutralized reaction mixture to a work-up involving washing and distillation,
wherein the separation of the water from the reaction mixture obtained in step a) comprises
  b.1) separating the reaction mixture obtained in step a) in a separating container into an aqueous and an organic phase (1a), and then
  b.2) passing the aqueous phase obtained in step b.1) through a filter bed of coalescence fiber material and then separating the aqueous phase obtained thereby into an aqueous phase and an organic phase (1b), and then
  b.3) combining the organic phase (1b) obtained in step b.2) with the organic phase (1a) obtained in step b.1) to give the organic phase (1).

2. The process as claimed in claim 1, in which the fiber diameter of the coalescence fiber material is 1.0 µm to 150 µm.

3. The process of claim 1, in which the fibers of the coalescence fiber material are prepared from a material selected from the group consisting of glass and organic polymer material.

4. The process of claim 3, in which the coalescence fiber material is selected from the group consisting of borosilicate glass and fluorine-containing organic polymer materials.

5. The process of claim 4, in which the fluorine-containing organic polymer material is selected from the group consisting of polytetrafluoroethylene (PTFE), polytrifluoroethylene, polydifluoroethylene, copolymers of tetrafluoroethylene and/or trifluoroethylene and/or difluoroethylene with one another and with other monomers, and derivatives of polytetrafluoroethylene.

6. The process of claim 5, in which the fluorine-containing organic polymer material is selected from the group consisting of polytetrafluoroethylene and derivatives of polytetrafluoroethylene.

7. The process of claim 1, in which the thickness of the filter bed of coalescence fiber material is 1.0 mm to 100 mm.

8. The process of claim 1, in which in step (b.2) the passing of the aqueous phase obtained in step (b.1) through the filter bed is carried out in the temperature range from 50° C. to 120° C.

9. A process for the preparation of di- and polyisocyanates of the diphenylmethane series by phosgenation of di- and polyamines of the diphenylmethane series prepared according to a process of claim 1.

* * * * *